United States Patent
Puschner et al.

(10) Patent No.: US 6,926,809 B2
(45) Date of Patent: Aug. 9, 2005

(54) DEVICE AND PROCESS FOR THE PURIFICATION OF CYANURIC CHLORIDE

(75) Inventors: Kurt Puschner, Rodenbach (DE); Stephanie Schauhoff, Frankfurt (DE)

(73) Assignee: Degussa AG, Hanau-Wolfgang (DE)

( * ) Notice: Subject to any disclaimer, the term of this patent is extended or adjusted under 35 U.S.C. 154(b) by 293 days.

(21) Appl. No.: 10/142,833

(22) Filed: May 13, 2002

(65) Prior Publication Data

US 2002/0195328 A1 Dec. 26, 2002

(30) Foreign Application Priority Data

May 11, 2001 (DE) .......................................... 101 23 072

(51) Int. Cl.[7] .............................. B01D 3/42; B01D 5/00; C07D 251/28
(52) U.S. Cl. ................................. 203/1; 203/2; 203/87; 544/190; 544/191
(58) Field of Search .......................... 203/1, 2, 87, 100; 202/160, 186; 544/190, 191

(56) References Cited

U.S. PATENT DOCUMENTS

| | | | | |
|---|---|---|---|---|
| 3,925,377 A | * | 12/1975 | Geiger et al. | 544/191 |
| 4,038,276 A | * | 7/1977 | Geiger et al. | 544/191 |
| 4,245,090 A | * | 1/1981 | Goedecke et al. | 544/191 |
| 4,245,091 A | * | 1/1981 | Goedecke et al. | 544/191 |
| 4,245,092 A | * | 1/1981 | Goedecke et al. | 544/191 |

FOREIGN PATENT DOCUMENTS

| | | |
|---|---|---|
| DE | 28 43 380 | 4/1980 |
| DE | 28 43 381 | 4/1980 |
| DE | 28 43 382 | 4/1980 |

* cited by examiner

Primary Examiner—Virginia Manoharan
(74) Attorney, Agent, or Firm—Oblon, Spivak, McClelland, Maier & Neustadt, P.C.

(57) ABSTRACT

The present invention relates to a device and method for the production of cyanuric chloride. The device has three units for the production, purification and isolation of cyanuric chloride, the second unit having a partial condensation and being set in such a way that the quantity of gaseous pure cyanuric chloride produced is greater than that of the liquid impure cyanuric chloride discharged from it.

5 Claims, 1 Drawing Sheet

DEVICE AND PROCESS FOR THE PURIFICATION OF CYANURIC CHLORIDE

BACKGROUND OF THE INVENTION

1. Field of the Invention

The present invention relates to a method and a device for the production of cyanuric chloride. In particular, the invention relates to a device in which cyanuric chloride is synthesized in a first unit, purified in a second unit and isolated in a third unit.

2. Discussion of the Background

Cyanuric chloride has the formula:

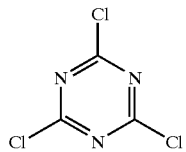

and is the trimerisation product of cyanogen chloride. This compound is an interesting and useful intermediate for further industrial processing to produce dyes, products for the textile industry as well as pharmaceuticals and plant protection agents, for example.

The specifications DE2843381 and DE2843380 disclose a device and a process for the production of cyanuric chloride in which, after trimerising cyanogen chloride, the reaction gas mixture is fed into a column equipped with a condenser at the upper end. According to this process, the condenser temperature should be below the boiling point of cyanuric chloride (146–190° C.) and the reaction gas should be fed in in the middle of the column. At the bottom of this column is a heating device in which liquid cyanuric chloride is continuously converted to the gaseous state. At the same time, the column disclosed here also has a discharge outlet at its lower end, through which liquid material can be withdrawn from the system. At the upper end of the column, a device is provided for drawing off gaseous cyanuric chlorid with an attached desublimation and isolation device. However, the teaching of this document relates to the aspect that the quantity of liquid cyanuric chloride discharged at the bottom of the column is proportionately greater than that of the gaseous cyanuric chloride drawn off through the condenser. This is emphasised by the prescribed condenser temperature of less than 190° C., which prohibits greater discharge of gaseous cyanuric chloride.

The quality of a process for the production of cyanuric chloride is measured substantially by the quality of the product produced and the given economic and ecological boundary conditions under which the product is obtained.

Thus, the flowability and purity of the cyanuric chloride obtained are important specification criteria, particularly for its use for the production of pharmaceuticals. Furthermore, the residence time of the carbon used for trimerization of cyanogen chloride to produce cyanuric chloride, amongst other things, is a decisive perameter for calculating the costs of the product, as each change causes cost-intensive stoppages, in which the apparatus cannot produce any product (DE19918245).

OBJECT OF THE INVENTION

Figure 1:
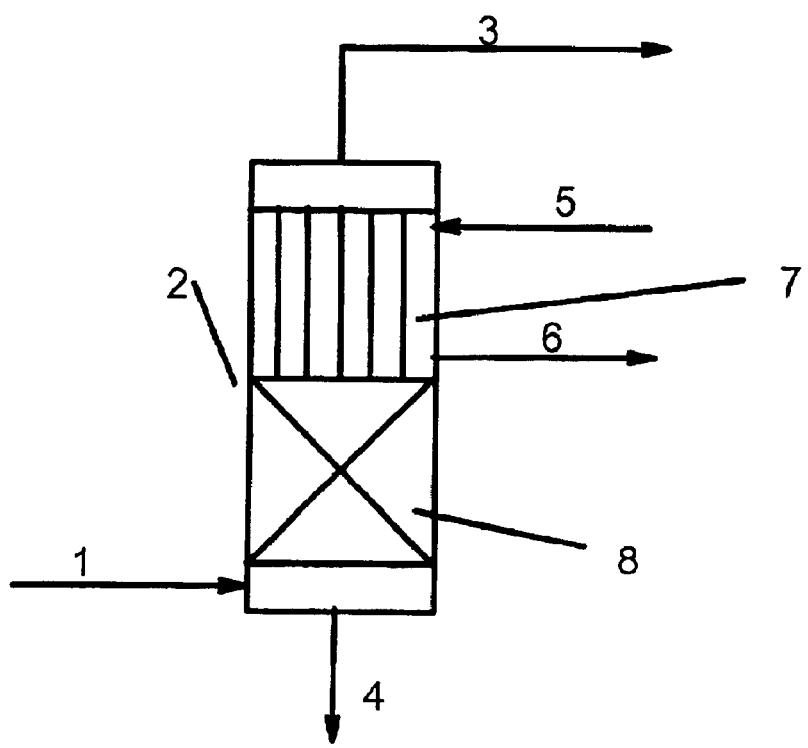
FIG. 1 shows a diagram of a second unit according to the invention with product streams.

The object of the present invention was therefore to provide another device, and method, which takes optimum account of all of the points mentioned above.

DETAILED DESCRIPTION OF THE INVENTION

These and other objects not mentioned are achieved by a unique device, and a process carried out in this device under certain conditions.

That is, by using a device for the production of cyanuric chloride having a first unit for the trimerisation of cyanogen chloride, a second unit for the partial condensation of the cyanuric chloride and a third unit for the desublimation and/or condensation of the gaseous cyanuric chloride, feeding a reaction gas stream from the first unit into the lower part of the second unit, which has a quenching column with a condenser at the upper end and a discharge outlet at the lower end, drawing off the gaseous cyanuric chloride mixture that is passed through the condenser area and then desublimated and/or condensed in the third unit, the condenser of the second unit being set at a temperature at which more cyanuric chloride is drawn off in the gaseous state than is discharged at the bottom of the quenching column in the condensed state, high yields of a consistently high quality of optionally solid or liquid cyanuric chloride are obtained in a surprisingly simple, but no less advantageous, way.

The device described herein allows the ratio of pure gaseous to impure liquid cyanuric chloride to be set as variable by regulating the condensation temperature. This fact, known already from DE2843381 and DE2843380, is, however, modified by setting the condenser at a temperature at which it is determined that more cyanuric chloride is drawn off in the gaseous state than is discharged in the condensed state at the bottom of the quenching column, which cannot be deduced from the teaching of the specifications mentioned above. Precisely because of this modification according to the invention, a solid or optionally liquid product is obtained, which firstly has greater purity than the liquid material obtained in DE2843380 and DE2843381, and secondly this can be kept at a consistently good level over the residence time of the carbon, by variable setting of the condensation temperature. In addition, the device according to the invention tolerates a reaction gas stream containing more impurities from the first unit than is possible in the prior art with comparable quality, as the unwanted secondary components are depleted surprisingly effectively in the second unit. Thus the residence time of the carbon used for the trimerization can be increased at the same time, which is advantageous for production costs, as mentioned at the beginning.

As already mentioned, the condenser temperature can be regulated individually, although it must be set in such a way that more cyanuric chloride is drawn off in the gaseous state from the second unit than is discharged in the condensed state at the bottom of the quenching column. However, the temperature selected should preferably not be too high, as the high-boiling portion in particular, consisting substantially of cyameluric chloride, bis-2,6-dichloro-s-triazinyl, tetrameric cyanogen chloride, 2,4,5,6 tetrachloropyrimidine and 2-cyanodichlorotriazine, increases in the gaseous product drawn off as the condenser temperature rises. In general, condenser temperatures should be set at a value>the boiling temperature of cyanuric chloride at ambient pressure, preferably >193° C. and <200° C. A temperature range of >194° C. and <198° C. is preferred in particular.

A person of ordinary skill in the art can choose how to combine the different units of the invention device in view of this disclosure, provided the function carried out according to the invention. Thus, it may be advantageous to provide other devices for purifying (A-carbon filter), subsequent reaction, temperature setting (heat exchanger) etc. between the first and second unit of the device according to the invention, which help to further increase the product purity and yield. However, the embodiment in which the reaction gas stream is fed directly from the first unit into the second unit is preferred. The reason for this is that, on leaving the first unit, the said stream is heated in such a way that, when fed directly into the second unit, it is at a temperature of 300° C. This heats the mixture at the bottom of the second unit (quenching column) to the point where the liquid cyanuric chloride is converted continuously to the gas phase. This preferred process thus makes it possible to form the second unit in such a way that it needs no additional source of heat. The advantage of this device from an apparatus point of view is clear, as this measure of course renders an additional source of heat at the bottom of the quenching column, as disclosed in DE2843380 and DE2843381, superfluous.

As already mentioned, the gaseous cyanuric chloride fed through the condenser should exceed the quantity of the product to be discharged at the bottom of the quenching column. In this range, the ratio can be set by the person skilled in the art in view of this disclosure using the measures described, however the quantity ratio should be set in such a way that a consistently high degree of purity of the cyanuric chloride desired according to the invention is obtained. In particular, the quantity ratio of cyanuric chloride drawn off in the gaseous state to that discharged at the bottom of the quenching column should preferably be 90:10 to 99.9:0.1, more preferably 98:2 to 99:1.

The device according to the invention is thus preferably operated in such a way that the trimerisation reaction takes place in a first unit. This first unit can be arranged according to the features familiar to the person skilled in the art in view of this disclosure, and is preferably identical to the apparatus mentioned or cited in DE 19918245. The reaction gas stream leaving the first unit is then preferably fed directly into the bottom of the second unit. FIG. 1 shows a diagram of the second unit with the product streams. The hot reaction gas brings the mixture at the bottom of the second unit (quenching column) to boiling point, wherupon cyanuric chloride is preferably converted into the gas phase. The gas mixture rising up the quenching column, which is rich in cyanuric chloride and burdened with high-boiling constituents, partially condenses in the condenser, set at a temperature above the boiling point of cyanuric chloride, at the upper end of the quenching column, the majority of the very pure cyanuric chloride leaving the condenser in the gaseous state and being fed into the third unit of the device according to the invention, and a partially condensed stream, which is now relatively more rich in high-boiling constituents, flowing back to the bottom of the quenching column. In so doing it meets gaseous, hot reaction gas flowing up from the bottom, as a result of which proportionately more cyanuric chloride evaporates out of the downwards flow again, and flows to the condenser, than the reverse. Thus, with the minimum loss of cyanuric chlorid yield and the minimum expenditure on apparatus, the maximum product purity is achieved.

The second unit can be arranged in a way known to the person skilled in the art, in view of this disclosure. Preferably, the quenching column is provided with packing, which increases the plate number for partial condensation and results in improved purification of the product stream. Other arrangements of the second unit such as dimensioning and, in particular, the type, fixing and design of the condenser part are left to the person skilled in the art. Such things can also be taken from the literature (Grundoperationen chemischer Verfahrenstechnik, [Basic Operations of Chemical Process Technology] Vauck/Müller 8th Edition 1988, pg. 490–493; Wärmeatlas,[Heat Atlas] 5th Edition, 1988, pg. Cb8-8 or Jal-Je20).

The third unit, into which the cyanuric chloride stream is fed, preferably in the gaseous state, for desublimation and/or condensation, can also be formed as desired by the person skilled in the art in view of this disclosure. Ideas for the arrangement can be taken for example from DE2843380 and DE2843381. Ullmann, 1996, Vol.3, 2-18, 2-88, 3-29,2-85, 5-5, Ullmann Vol. 2,page 664–671, 1972 Edition or Perry Chemical Engineers Handbook, 4th Imprint, 1964 Edition, Chapter 17-23 to 17-26 and EP137505 disclose successful desublimation and condensation apparatus.

Overall, the device helps in many ways to ensure more efficient and thus more cost-effective production of cyanuric chloride coupled with improved purity. In particular, the fact that in spite of increasing the condenser temperature to above that stated in DE2843381 and DE2843380, product purity is not diminished below specification limits, means that on the one hand, a continuously high yield is achieved with consistently good product purity and on the other the residence time of the catalyst for the trimerisation reaction is increased. All of this was by no means obvious at the the time of the invention.

In addition to the high-boiling consitutents described, which are present in the reaction gas stream, it also contains compounds which boil at a lower temperature than cyanuric chloride. It is clear that these leave the condenser of the second unit together with the gaseous cyanuric chloride. These components are then separated in the desublimation and/or condensation unit according to the method familiar to the person skilled in the art (DE2843381 and DE2843380, EP137505).

Detailed Description of FIG. 1:

The hot reaction gas stream passes from the first unit through a feed (1) into the second unit (quenching column 2). The cyanuric chloride flows through the column part (8) of the quenching column, until it meets the condenser (7). This is supplied, through line (5), with a cooling liquid at a corresponding temperature, which can flow off again through line (6). The condensed part of the gas stream flows down to the bottom of (2) and is removed from the column (2) through the discharge outlet (4). At the top of (2) the cyanuric chloride is fed on into the third unit through line (3).

EXAMPLES 1) 4.4 kg/h cyanuric chloride vapour at a temperature of 280° C. are fed into the quenching column. The concentration of high-boiling by-products is 0.41 wt. %, which corresponds to a flow of ca 0.018 kg/h.

A set temperature of 194° C. for partial condensation, produces a liquid discharge quantity of 1.42 kg/h with a by-product content of 1.15 wt. %, corresponding to a by-product flow of ca 0.016 kg/h (90%).

2) Partial condensation at 197° C. is carried out according to example 1. A liquid discharge quantity of 0.66 kg/h with a by-product content of 2.41 wt. % is obtained. This also corresponds to a by-product flow of 0.016 kg/h (90%).

German patent application 101 23 072.9 is incorporated hearin by reference, as are all specifications, articles, texts, references and patents referred to above.

What is claimed is:

1. A method for the production of cyanuric chloride, comprising trimerizing cyanogen chloride in a first unit which is a reactor unit, to produce a reaction gas stream containing gaseous cyanuric chloride and gaseous impurities, partially condensing the cyanuric chloride in the reaction gas stream produced in the first unit in a second unit, and desublimating and/or condensing gaseous cyanuric chloride from the second unit in a third unit, wherein the reaction gas stream from the first unit is fed into a lower area of the second unit, said second unit having a quenching column through which the gases rise, a condenser at an upper end to cool the gases from the quenching column passing into it and a discharge outlet at a lower end, determining the quantity of cyanuric chloride being discharged in the condensed state from the second unit and that which is drawn off in the gaseous state through the condenser of the second unit and setting the temperature of the condenser of the second unit so that more cyanuric chloride is drawn off in the gaseous state than is discharged in the condensed state at the bottom of the quenching column, the second unit arranged such that gaseous cyanuric chloride mixture which has been passed through the condenser area may be drawn off for desublimation and/or condensation in the third unit, the temperature of the condenser in the second unit being set at a value greater than the boiling point of the cyanuric chloride at ambient pressure, and wherein the temperature of the gases in the reaction gas stream fed into a lower area of the second unit is high enough to bring the mixture at the bottom of the quenching column to the boiling point.

2. The method according to claim 1, wherein the reaction gas stream is fed directly from the first unit into the second unit.

3. The method according to claim 1, wherein the second unit has no external source of heat.

4. The method according to claim 1, wherein the mass ratio of cyanuric chloride drawn off in the gaseous state to that discharged at the bottom of the quenching column is 90:10 to 99.9:0.1.

5. The method according to claim 1, wherein the mass ratio of cyanuric chloride drawn off in the gaseous state to that discharged at the bottom of the quenching column is 98:2 to 99:0.1.

* * * * *